US011099204B2

(12) United States Patent
Proano et al.

(10) Patent No.: US 11,099,204 B2
(45) Date of Patent: Aug. 24, 2021

(54) FREE-FALL AND IMPACT DETECTION SYSTEM FOR ELECTRONIC DEVICES

(71) Applicant: Varex Imaging Corporation, Salt Lake City, UT (US)

(72) Inventors: Cesar H Proano, Palo Alto, CA (US); Rudiger Schwartz, Santa Clara, CA (US)

(73) Assignee: Varex Imaging Corporation, Salt Lake City, UT (US)

( * ) Notice: Subject to any disclaimer, the term of this patent is extended or adjusted under 35 U.S.C. 154(b) by 0 days.

(21) Appl. No.: 16/147,519

(22) Filed: Sep. 28, 2018

(65) Prior Publication Data

US 2020/0103434 A1 Apr. 2, 2020

(51) Int. Cl.
| | | |
|---|---|---|
| G01C 3/02 | (2006.01) | |
| G01P 15/08 | (2006.01) | |
| A61B 6/10 | (2006.01) | |
| A61B 6/00 | (2006.01) | |

(52) U.S. Cl.
CPC .......... *G01P 15/0802* (2013.01); *A61B 6/102* (2013.01); *A61B 6/4405* (2013.01); *G01C 3/02* (2013.01)

(58) Field of Classification Search
CPC .................................................. G01P 15/0802
USPC ......................................................... 73/510
See application file for complete search history.

(56) References Cited

U.S. PATENT DOCUMENTS

| | | | | |
|---|---|---|---|---|
| 7,059,182 | B1* | 6/2006 | Ragner | H05K 5/0086 73/200 |
| 10,572,270 | B1* | 2/2020 | Sampath | G06F 9/4418 |
| 2008/0174444 | A1* | 7/2008 | Noda | G01P 15/08 340/669 |
| 2011/0254792 | A1* | 10/2011 | Waters | G06F 1/1626 345/173 |
| 2011/0275356 | A1* | 11/2011 | Best | H04W 36/385 455/414.1 |
| 2012/0206414 | A1* | 8/2012 | Tada | G06F 1/1643 345/175 |
| 2013/0257582 | A1* | 10/2013 | Rothkopf | G06F 1/1656 340/3.1 |
| 2014/0039828 | A1* | 2/2014 | Kasama | G01P 15/0891 702/141 |
| 2015/0221278 | A1* | 8/2015 | Le Grand | G06F 1/3265 345/156 |
| 2015/0289365 | A1* | 10/2015 | Hunat | H01L 23/13 257/459 |
| 2016/0218555 | A1* | 7/2016 | Slaby | H04W 52/0254 |
| 2016/0220153 | A1* | 8/2016 | Annegarn | A61B 5/1117 |
| 2017/0023696 | A1* | 1/2017 | Morton | G01V 5/0025 |
| 2018/0054502 | A1* | 2/2018 | Wilson | G06F 1/1694 |
| 2019/0020822 | A1* | 1/2019 | Sharma | G02B 27/646 |

\* cited by examiner

*Primary Examiner* — Jamel E Williams
(74) *Attorney, Agent, or Firm* — Laurence & Phillips IP Law

(57) ABSTRACT

Some embodiments include a handheld detector, comprising: detector circuitry configured to convert incident radiation into electrical signals; a processor coupled to the detector circuits; and an accelerometer coupled to the processor; wherein the processor is configured to activate from a low power state in response to a first acceleration event detected by the accelerometer.

17 Claims, 6 Drawing Sheets

FREE-FALL AND IMPACT DETECTION SYSTEM FOR ELECTRONIC DEVICES

BACKGROUND

Electronic devices and, in particular, handheld electronic devices may be subject to impacts due to accidents, mishandling, intentional acts, or the like. Devices may be designed to withstand an impact with a particular magnitude. However, when a device has been affected by an impact, it may be difficult to determine the cause of the impact. Handheld flat panel detectors, such as those used in x-ray diagnostic systems, may be particularly susceptible to impacts as the handheld detectors may be transported from location to location by a user.

DETAILED DESCRIPTION

This disclosure relates to free-fall and impact detection systems for electronic devices and, in particular, to free-fall and impact detection systems for handheld radiation or X-ray detectors.

Electronic devices, such as flat panel and flexible X-ray detectors, are becoming more portable. With that portability comes an increased risk of physical abuse. Some devices may be designed to continue to operate after an impact on a specified material from a specified height. For example, the device may continue to operate even when dropped from a height of 1 meter (m) on to concrete. However, without knowing how high the panel was dropped from or what gravitational force (g-force) it experienced it may be difficult to determine if the specified rating was exceeded. In addition, information related to physical impacts may be used to diagnose problems, determine what kind of abuse the device has suffered, collect data for future designs, or the like.

Figure 1A:
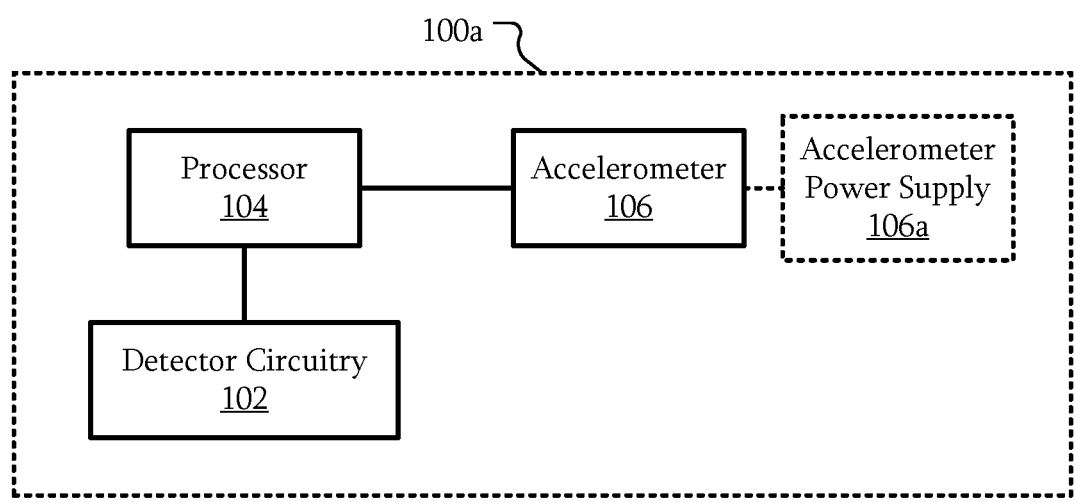
FIG. 1A is a block diagram of a detector with an accelerometer according to some embodiments.

Various embodiments of detectors 100 will be described below. FIG. 1A is a block diagram of a detector with an accelerometer according to some embodiments. The detector 100a includes detector circuitry 102, a processor 104, and an accelerometer 106. The detector circuitry 102 includes circuitry such as pixels of a detector, readout circuitry, control circuitry, or the like. The detector circuitry 102 may include an array of pixels. In some embodiments, the detector circuitry 102 may include a scintillator. The detector circuitry 102 may be configured to convert incident radiation, such as x-rays or light, into electrical signals. In some embodiments, the electrical signals may be processed to form an image.

The processor 104 may be a general purpose processor, a digital signal processor (DSP), an application specific integrated circuit, a microcontroller, a programmable logic device, discrete circuits, a combination of such devices, or the like. The processor 104 may include internal portions, such as registers, cache memory, processing cores, or the like, and may also include external interfaces, such as address and data bus interfaces, interrupt interfaces, or the like. Although only one processor 104 is illustrated in the detector 100a, multiple processors 104 may be present. In addition, other interface devices, such as logic chipsets, hubs, memory controllers, communication interfaces, or the like may be part of the detector 100a to connect the processor 104 to internal and external components. Furthermore, the processor 104 may be coupled to memory such as a dynamic random access memory (DRAM) module, a double data rate synchronous dynamic random access memory (DDR SDRAM) according to various standards such as DDR, DDR2, DDR3, DDR4, static random access memory (SRAM), non-volatile memory such as Flash, spin-transfer torque magentoresistive random access memory (STT-MRAM), or Phase-Change RAM, magnetic media, or the like. Information collected and/or results of operations described herein may be stored in the memory.

The processor 104 may be coupled to the detector circuitry 102 and the accelerometer 106. The processor 104 may be configured to control operations of the detector circuitry 102 and communicate with the accelerometer 106. However, in other embodiments, the processor 104 may be a separate processor coupled to the accelerometer 106 and another processor may control some or all of the detector circuitry 102. The processor 104 may communicate with other circuitry of the detector 100a to perform operations described herein.

The accelerometer 106 is a device configured to sense acceleration. In some embodiments, the accelerometer 106 may be a single axis accelerometer; however, in other embodiments, the accelerometer 106 may be a three-axis accelerometer. The accelerometer 106 may be configurable to sense a free-fall event. For example, the accelerometer 106 may have a configurable threshold such that, when an acceleration event exceeds the threshold, the accelerometer 106 generates an interrupt on an interrupt line coupled to the processor 104. In some embodiments, the accelerometer 106 may include circuitry to generate an interrupt; however, in other embodiments, external circuitry may be used to read the accelerometer state and determine if an interrupt should be generated. The accelerometer 106 may be a low power accelerometer.

In some embodiments, the accelerometer 106 may have a measurement range that is significantly less than an acceleration due to an expected impact. For example, the measurement range of the accelerometer 106 may be +/−2 g, 8 g, 16 g, or the like while an expected impact may be on the order of 1000 g. However, the accelerometer 106 has a measurement range that is sufficient to detect a change in acceleration to indicate a free-fall state of the detector 100a.

In some embodiments the accelerometer 106 may be powered from a main power supply (not illustrated) for the detector 100a. However, in other embodiments, the accelerometer 106 may be coupled to a dedicated accelerometer power supply 106a. The accelerometer power supply 106a may include a battery, a capacitor, or the like to supply power to the accelerometer 106 when the detector 100a is operating in a low power state. While the detector 100a is powered or recharging a battery of the main power supply, the accelerometer power supply 106a may be recharged. In some embodiments, the accelerometer 106 may be operating continuously, especially when the processor 104 is in an inactive state.

Figure 1B:
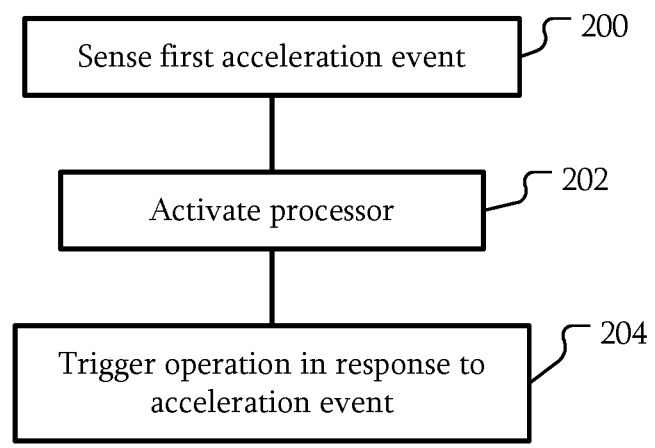
FIG. 1B is a flowchart illustrating operation of a detector with an accelerometer according to some embodiments.

FIG. 1B is a flowchart illustrating operation of a detector with an accelerometer according to some embodiments. Referring to FIGS. 1A and 1B, in some embodiments, in 200, a first acceleration event is sensed. An acceleration event is a change in the acceleration sensed by the accelerometer 106. An acceleration event may be a change in the acceleration that is greater than a threshold. In some embodiments, the acceleration event is a change in the magnitude of the acceleration; however, in other embodiments, acceleration event may also include a change in direction of the acceleration. In some embodiments, the acceleration event may be an increase in the acceleration, such as a downward acceleration where the acceleration exceeds normal gravity.

The first acceleration event may occur while the processor 104 is in a low power state such as an inactive state, a sleep state, a reduced performance state, or the like, where the processor 104 is using less than full operating power. The accelerometer 106 may detect a change in acceleration such as a change from normal gravity to a free-fall state. Accordingly, in 202, the processor 104 is activated (e.g., to an operational state) in response to the first acceleration event. For example, the accelerometer 106 may generate an interrupt on an interrupt line coupled between the accelerometer 106 and the processor 104. The processor 104 may enter an active state, leave the sleep state, or the like in response to the interrupt. Thus, the processor 104 may be activated in response to acceleration event.

In 204, an operation is triggered in response to the acceleration event. As will be described in further detail below, a variety of operations may be performed. In some embodiments, more than one operation may be triggered in response to a single acceleration event. In some embodiments, operations triggered in response to the acceleration event may also depend on a second acceleration event after the first acceleration event. In some embodiments, the triggering of the operation in 204 may occur for each acceleration event.

The processor 104 may be configured to record data from the acceleration event, the triggered operation, and/or contemporaneous information available to the processor 104. For example, the processor 104 may be configured to store a magnitude and/or direction of the acceleration event, information from before, during, and after the triggered operation, or the like. The processor 10 may be configured to store the data in a memory in association with the acceleration event.

Figure 2A:
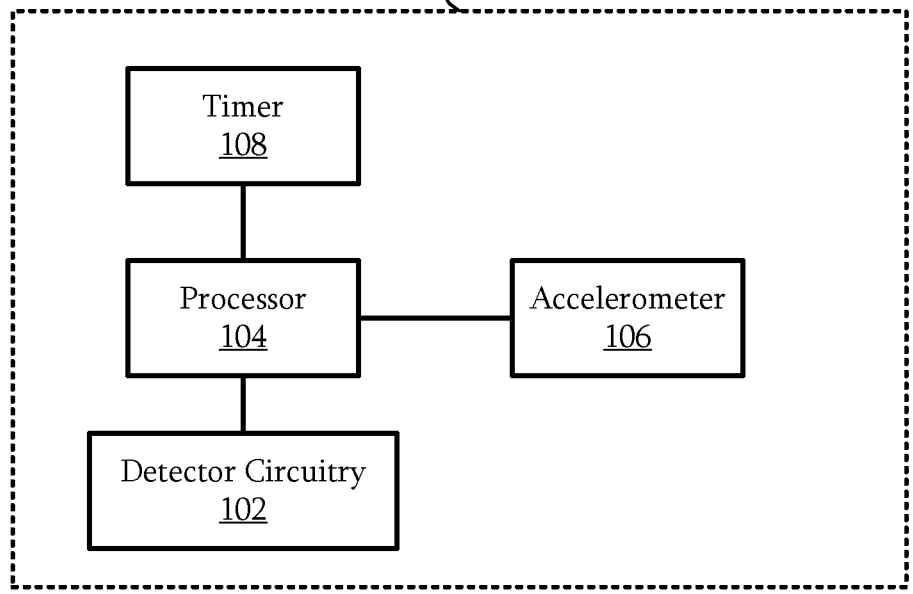
FIG. 2A is a block diagram of a detector with an accelerometer and a timer according to some embodiments.

FIG. 2A is a block diagram of a detector with an accelerometer and a timer according to some embodiments. The detector 100b may be similar to the detector 100a of FIG. 1A. However, the detector 100b includes a timer 108. The timer 108 may be an external component coupled to the processor 104; however, in other embodiments, the timer 108 may be an internal component of the processor 104, a software implemented timer, or the like.

Figure 2B:
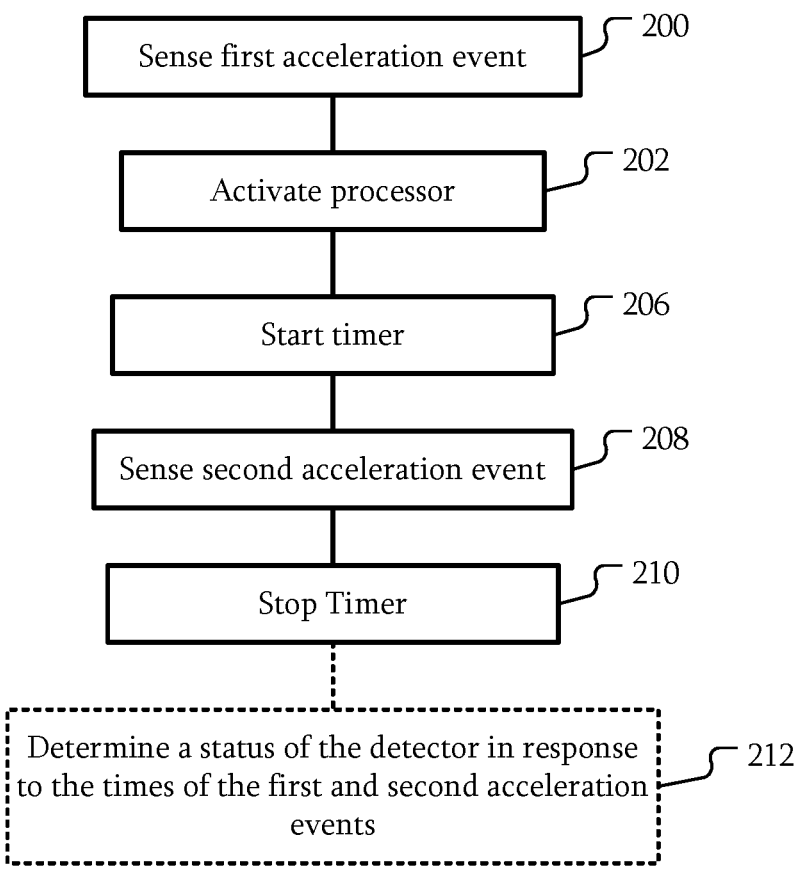
FIG. 2B is a flowchart illustrating operation of a detector with an accelerometer and a timer according to some embodiments.

FIG. 2B is a flowchart illustrating operation of a detector with an accelerometer and a timer according to some embodiments. Referring to FIGS. 2A and 2B, operations 200 and 202 may be similar to that described above with respect to FIG. 1B.

In 206, the timer 108 is started. For example, once the processor is activated in 202, the processor 104 may cause the timer 108 to begin counting.

In 208, a second acceleration event is detected. For example, the accelerometer 106 may generate another interrupt as described above in response to the second acceleration event. In a particular example, the second acceleration event may be an impact event when the detector 100b contacts the floor, another surface, or the like.

In 210, the timer is stopped. A value of the timer 108 may be read by the processor 104 to obtain the time between the first and second acceleration events. While starting the timer 108 and stopping the timer 108 have been used as example, time may be tracked in different manners. For example, starting the timer 108 in 206 may include the processor 104 reading a value of the timer 108 and storing that value in memory as a start time. Stopping the timer 108 in 210 may include the processor 104 reading a value of the timer 108 and storing that value in memory as a stop time. The start time and stop time may be used by the processor 104 to calculate the time between the first and second acceleration events.

In some embodiments, the processor 104 may merely record the data from the timer 108. However, in other embodiments, in 212, a status of the detector 100b may be determined in response to the times of the first and second acceleration events. The status may include information such as how many times the detector 100b has entered free-fall, whether the fall distance exceeded a specified limit, or the like. Additional information may also be recorded as part of the status, such as the number and magnitude of impacts, whether the magnitude of the impact exceeded a specified limit, an indication of whether an acceleration was characterized an impact, or the like. For example, the difference between the times or a time the timer 108 was operated may be transformed into a distance. The distance calculation may use acceleration information from the first and second acceleration events. The time and/or the calculated distance may be stored in memory by the processor 104.

In a particular example, the processor 104 may be configured to determine a fall distance after the detector 100b was dropped, thrown, or the like. In some embodiments, the distance may be used to determine whether the detector 100b was operated within specified limits. For example, if a specified operation for the detector 100b included a drop of 1 meter onto a surface and the time and/or distance indicated a drop of 2 meters, the recorded data indicates that the detector 100b was operated outside of the specified limit. The time and/or the calculated distance may be used to set a flag or store information indicating whether the detector 100b has experienced a fall that exceeds that specified value.

In some embodiments, the first acceleration event and the second acceleration event may be sequential acceleration events. However, in other embodiments, the first and second acceleration events may not be sequential. For example, impacts that occur while a detector 100*b* is falling, such as impacts on a wall, table, stairs, or the like may cause intervening acceleration events between the first and second acceleration events. Times of the events, times between any pair of the acceleration events, or the like may be determined as described above. In some embodiments, the processor 104 may determine which of subsequent acceleration events will be handled as the second acceleration event as described above. For example, the second acceleration event may be the first of a series of acceleration events due to the detector 100*b* bouncing on the floor after being dropped.

Although particular techniques of operating a timer 108 and processor 104 have been used as example, in other embodiments, a free-fall time may be determined using different techniques.

Figure 3A:
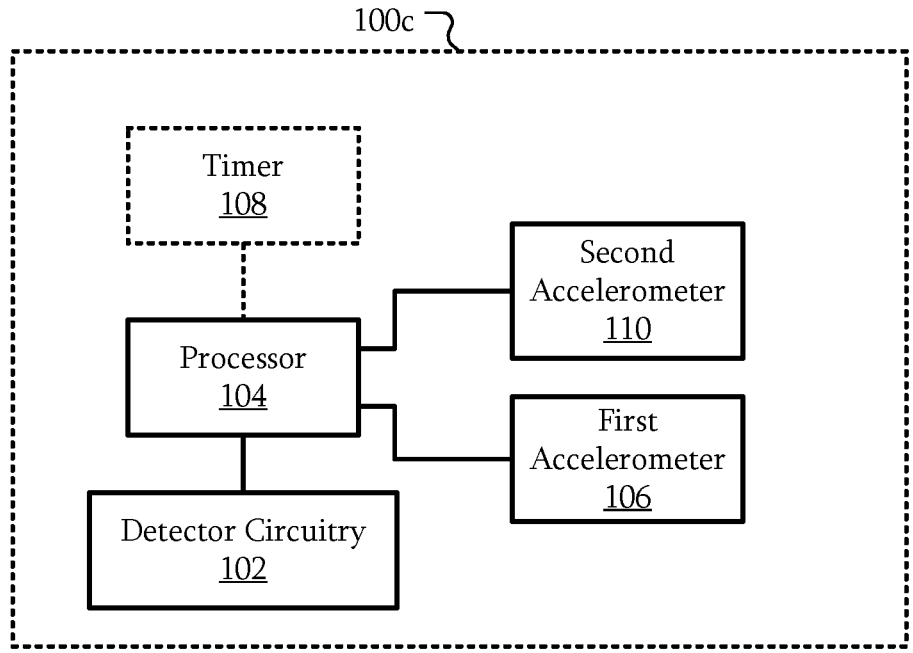
FIG. 3A is a block diagram of a detector with an accelerometer and a higher power accelerometer according to some embodiments.

FIG. 3A is a block diagram of a detector with an accelerometer and a higher power accelerometer according to some embodiments. The detector 100*c* may be similar to the detectors 100*a* and 100*b* described above. However, the detector 100*c* includes a second accelerometer 110. The second accelerometer 110 has a measurement range defining magnitudes of acceleration that the second accelerometer can detect. That measurement range is greater than that of the first accelerometer 106. For example, the second accelerometer 110 may have a measurement range of +/−400 g in contrast to a +/−16 g measurement range or less of the first accelerometer 106.

In addition, the second accelerometer 110 may have a higher power consumption, higher sensitivity, and/or higher resolution than the first accelerometer 106. For example, the first accelerometer 106 may operate with a relatively low current of 10 microamps (µA). The second accelerometer 110 may operate with a higher current of 300 µA.

Figure 3B:
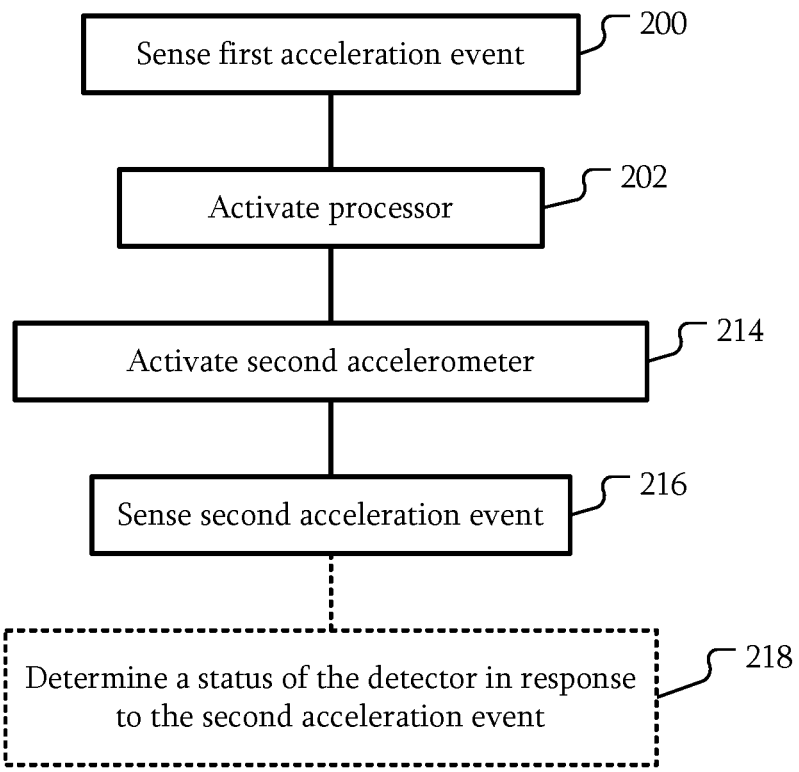
FIG. 3B is a flowchart illustrating operation of a detector with an accelerometer and a higher power accelerometer according to some embodiments.

FIG. 3B is a flowchart illustrating operation of a detector with an accelerometer and a higher power accelerometer according to some embodiments. Referring to FIGS. 3A and 3B, the operations in 200 and 202 may be similar to those described above. In 214, the second accelerometer 110 was activated in response to the first acceleration event. For example, once the processor 104 is activated in 202, the processor 104 may cause power to be supplied to the second accelerometer 110, cause the second accelerometer to exit a standby state and enter an operating state, or the like.

In 216, a second acceleration event may be sensed by the second accelerometer 216. This second acceleration event may provide additional information that the first accelerometer was not able to do so because of its smaller measurement range. For example, the second accelerometer 216 may provide the acceleration due to the impact. In some embodiments, the impact may exceed the measurement range of the second accelerometer 110. Thus, the second acceleration event may indicate that the impact caused the second accelerometer 110 to exceed its measurement range. In some embodiments, a measurable acceleration may indicate that an impact exceeding specification has occurred. However, in other embodiments, an impact that exceeds specification may be larger than the second accelerometer 110 may be capable of measuring.

Similar to the second acceleration event from the first accelerometer 106, information related to the second acceleration event from the second accelerometer 110 may be stored in memory by the processor 104. In addition, similar to the operation in 212 described above, the processor 104 may use the information from the second acceleration event from the second accelerometer 110 in 218 to determine a status of the detector 100*c*. For example, the acceleration event from the second accelerometer 110 may be characterized as an impact if the magnitude exceeds a threshold, characterized as an impact that exceeded a specified limit, or the like. The status of the detector 110*c* may include such information.

In some embodiments, a thickness of the detector 110*c* may limit a size of the second accelerometer 110. For example, the detector 100*c* may have a maximum thickness of about 10 millimeters (mm), about 15 mm, or the like. Accelerometers that fit within the detector 100*c* may need to have a smaller thickness. For example, other components, glass, base plates, circuit boards, or the like may use portions of the total thickness. A remaining thickness for the accelerometers may be about 5-6 mm. Accelerometers with measurement ranges at or above +/−1000 g may not be available in a size that fits within the thickness constraint. Such accelerometers may have thicknesses of 20-30 mm or greater. Mechanical sensors do not result in consistent or reproducible results. Mechanical sensors may have a tolerance of +/−25% or +/−250 g for a +/−1000 g measurement range. Accordingly, the thickness of the detector may prevent the use of an accelerometer with sufficient measurement range to accurately detect the force of an impact.

In some embodiments, the operations described with respect to FIG. 2B may be performed by the detector 100*c* in parallel with the operations described in FIG. 3B. For example, once the processor is activated in 202, separate acceleration events may be sensed in 208 by the first accelerometer 106 and in 216 by the second accelerometer 110.

In some embodiments, the data from the first accelerometer 106 and the second accelerometer 110 may be used together. For example, the values may be compared to experimental results to determine a type of material on which the detector 100*c* impacted. As described above, the first accelerometer 106 may be used to determine a fall time or distance. The second accelerometer 110 may be used to determine a magnitude of an impact. By comparing the measured values to experimental data from impacts on various materials from various heights, a type of material may be determined. The magnitude of acceleration of the impact can differ based on the type of the material that the detector 100*c* impacts even with similar fall times or distances. For example, concrete, tile, linoleum, rubber, sand, and grass surfaces may have different magnitudes of acceleration. The experimental data may include the magnitudes of the acceleration for impacts on various materials at various heights. For example, the experimental data may include magnitudes of the acceleration for impacts on concrete from heights of 0.5, 1, 1.5, and 2 meters and impacts on linoleum from similar heights. The free-fall time may be converted into a distance. The distance and the magnitude of the impact detected by the second accelerometer 110 may be compared with the experimental data. For example, the distance may indicate a fall of 1.5 meters. However, the measured impact from the second accelerometer 110 may be closer to that of the experimental result from the 1.5 meter impact on linoleum rather than the 1.5 meter impact on concrete. Thus, the material the detector 110*c* impacted may be linoleum. Although two materials have been used as examples, in other embodiments, any number of materials may be part of the experimental data and compared with the measured data. In addition, while a determination of a single material may be made, in some embodiments, a determination of a set of likely materials may be made. For example, the two or more closest matches may be determined to be the possible materials.

In some embodiments, the data from the first accelerometer 106 and the second accelerometer 110 may be used to characterize the combined event. For example, if the first accelerometer 106 senses a relatively large acceleration as the first acceleration event and the second acceleration event from the second accelerometer 110 is larger than expected, the combined event may be characterized as the detector 100c being thrown rather than dropped.

In some embodiments, the combination of the first accelerometer 106 and the second accelerometer 110 may result in an improved battery performance for detecting impacts. For example, if a single accelerometer such as accelerometer 110 is used with a measurement range that approaches or encompasses the force of expected impacts, that accelerometer may have a higher power consumption than the first accelerometer 106. By using the first accelerometer 106 to cause the processor 104 to activate the second accelerometer 110, the second accelerometer 110 may be left in a low power state until the second accelerometer 110 is needed. As a result, the power consumption will be decreased, increasing the useful life of a battery or other power source used to power the accelerometers 106 and 110. While a higher measurement range accelerometer such as the second accelerometer 110 may have a lower power operating mode, that lower power mode has less precision. Using the combination of the accelerometers 106 and 110 allows for the higher power mode to be used by activating it after a first acceleration event.

A handheld detector 100 as described herein may be a relatively expensive device on the order of thousands of dollars or more. In a medical diagnostic setting, the handheld detector 100 is regularly moved by a user to be under a patient's body, such as under arms, legs, or the like. During use and during transportation from patient to patient, the handheld detector 100 may be dropped and possibly damaged. The first accelerometer 106 may be used to detect if the handheld detector 100 has been dropped and, in particular, how long or far the handheld detector 100 has dropped.

As a result, an additional or replacement specification of distance may be part of the specification for the handheld detector 100. That is, the handheld detector 100 may be specified to operate after a fall of 1 meter regardless of the surface. In another example, the handheld detector 100 may be specified to operate after a specified number of impacts from heights less than 1 meter. Such specifications using distance, count, time, or the like may be easier for a user to understand and/or less likely to be disputed rather than a specification using force, such as a limit of 500 g, or a particular material, such as a 1 meter drop on to a vinyl covered concrete surface.

Figure 4A:
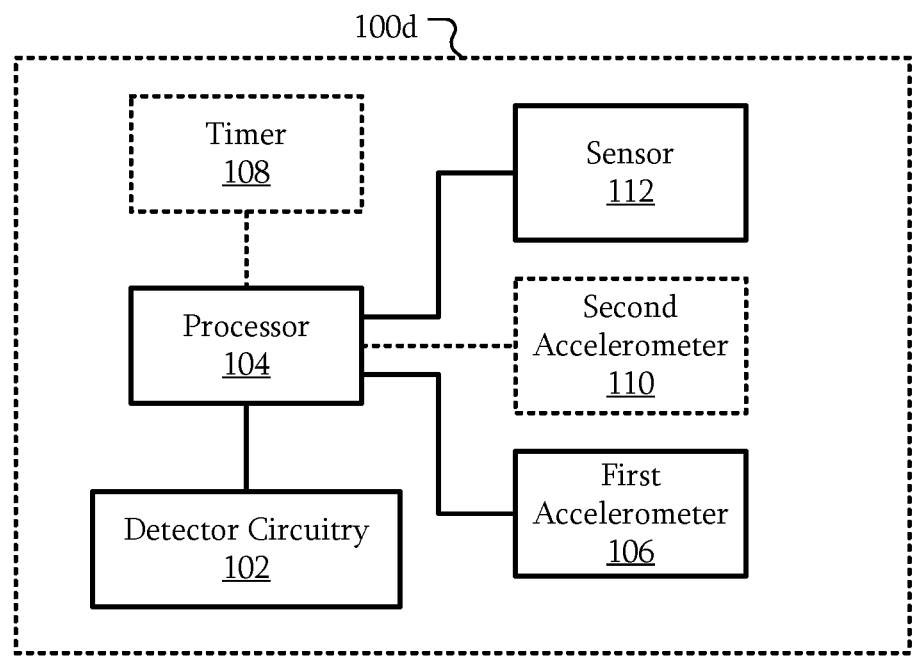
FIG. 4A is a block diagram of a detector with an accelerometer and one or more sensors according to some embodiments.

FIG. 4A is a block diagram of a detector with an accelerometer and one or more sensors according to some embodiments. The detector 100d may be similar to the detectors 100a-c described above. However, the detector 100d includes at least one sensor 112. The sensor 112 may include a temperature sensor, a humidity sensor, a gyroscope, a touch sensor, a rangefinder, or other types of sensors. Although one sensor 112 is illustrated, multiple sensors 112 may be part of the detector 100d, including multiple sensors 112 of the same or different types. The one or more sensors 112 may provide data on environmental conditions at or near a time when an impact occurs, a time when the detector 100d is in free-fall, or the like. For example, the temperature and/or humidity data may be used to determine if the temperature and/or humidity exceeded specified limits. A gyroscope may be used to record rotation of the detector 100d that may be used to diagnose damage to the detector 100d, such as whether the damage correlates with the measured rotation direction of the detector 100d.

Figure 4B:
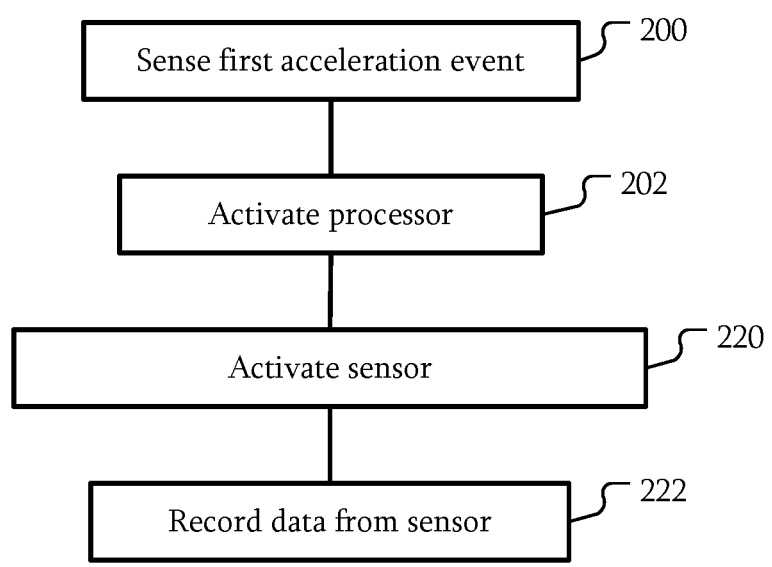
FIG. 4B is a flowchart illustrating operation of a detector with an accelerometer and one or more sensors according to some embodiments.

FIG. 4B is a flowchart illustrating operation of a detector with an accelerometer and one or more sensors according to some embodiments. The operation in 200 and 202 may be similar to that described above. In 220, a sensor 112 is activated. For example, the sensor 112 may be operating in a low power state. The processor 104 may activate the sensor 112 to operate in a normal or higher power state. In 222, data is recorded from the sensor 112. For example, the processor 104 may read one or more values from the sensor 112 and record those values to memory.

In some embodiments, the sensor 112 is a rangefinder such as an optical rangefinder, an ultrasonic rangefinder, or the like. Any device that may determine a range without contact may be used as the rangefinder. The sensor 112 may be activated in 220 and distance information may be obtained from the rangefinder in 222.

In some embodiments, the sensor 112 is a touch sensor. The touch sensor 112 may be mounted on the detector 100d such that the touch sensor 112 can detect if a user is holding the detector 100d. For example, the touch sensor may extend around a perimeter of the detector 100d, may be disposed in locations where a user is likely to hold the detector 100d. The output of the touch sensor 112 may be combined with data from the first accelerometer 106 to determined if the detector 100d has been dropped. For example, the touch sensor 112 could be used to interpret the first acceleration event as not in free-fall if the touch sensor 112 still indicates that the detector 100d is being held.

Figure 5A:
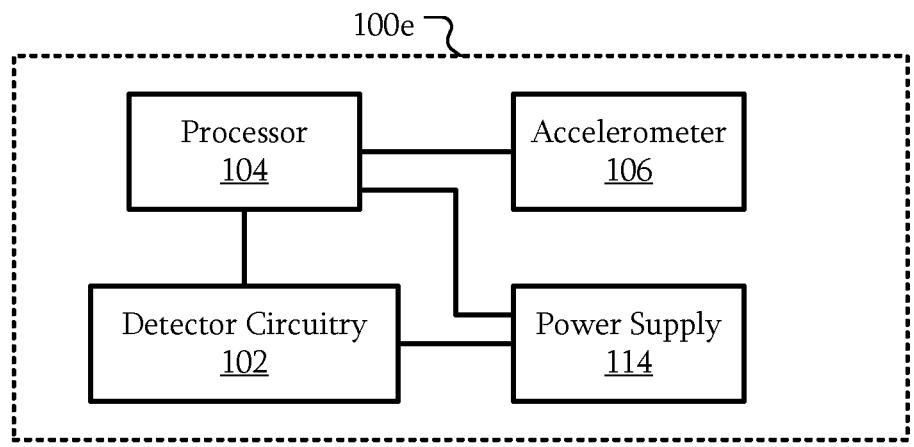
FIG. 5A is a block diagram of a detector with an accelerometer and a controllable power supply according to some embodiments.

FIG. 5A is a block diagram of a detector with an accelerometer and a controllable power supply according to some embodiments. The detector 100e may be similar to that of detectors 100a-d described above. However, in some embodiments, the detector 100e includes a power supply 114 that is responsive to an acceleration event. The power supply 114 may include a battery, capacitor, or the like used to power circuits of the detector 100e such as the detector circuitry 102.

Figure 5B:
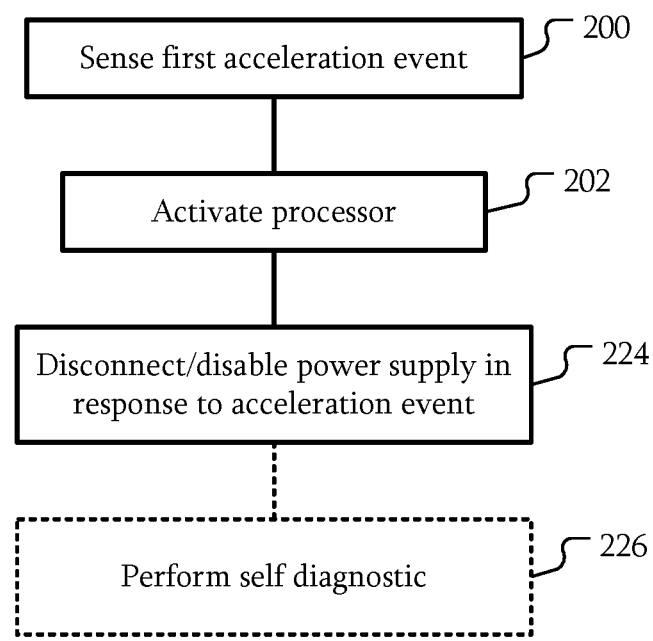
FIG. 5B is a flowchart illustrating operation of a detector with an accelerometer and a controllable power supply according to some embodiments.

FIG. 5B is a flowchart illustrating operation of a detector with and accelerometer and a controllable power supply according to some embodiments. Referring to FIGS. 5A and 5B, operations in 200 and 202 may be similar to those described above. In 224, the power supply 114 is disconnected or disabled in response to the first acceleration event. For example, the processor 104 may transmit a shutdown signal to the power supply 114, disable transistors in series with the power supply 114, set one or more voltages supplied by the power supply to zero or a lower voltage, or the like. In some embodiments, one or more of a battery, supercapacitor, or other energy storage device of the power supply 114 may be disconnected, isolating those energy storage devices from other circuitry of the detector 100e. As a result, power supplied may be disconnected or disabled.

In a particular example, active voltages in the detector circuitry 102 may cause a short or open on impact that may damage the detector circuitry 102. This damage may be in addition to the physical damage due to an impact. Such damage may be reduced or eliminated by disconnecting or disabling the power supply 114 before an impact. In some embodiments, less than all voltages suppled by the power supply 114 may be disconnected or disabled. For example, one or more voltages supplied to pixels of the detector circuitry may be disconnected or disabled while other voltages, such as those supplied to the processor 104, may be maintained.

In some embodiments, the conditions to cause the shutdown of the power supply 114 may include a time from the first acceleration event. For example, a timer may be started as described above. If the time tracked by the timer exceeds a threshold representing a maximum fall time or distance in which damage can occur, the power supply 114 may be disconnected or disabled. For example, the threshold may be a time that if the detector 100e stops falling or impacts an object before that time has elapsed, the damage due to the power supply 114 being activated will be minimal or not occur. The threshold may be a fraction, such as 1/10 or 1/4, of the time that would indicate a fall greater than a specified maximum.

After the power is disconnected or disabled in 224, the processor 104 may be configured to perform a self-diagnostic procedure in 226. For example, the processor 104 may check the power supply voltages, communication with internal components or the like.

Figure 6:
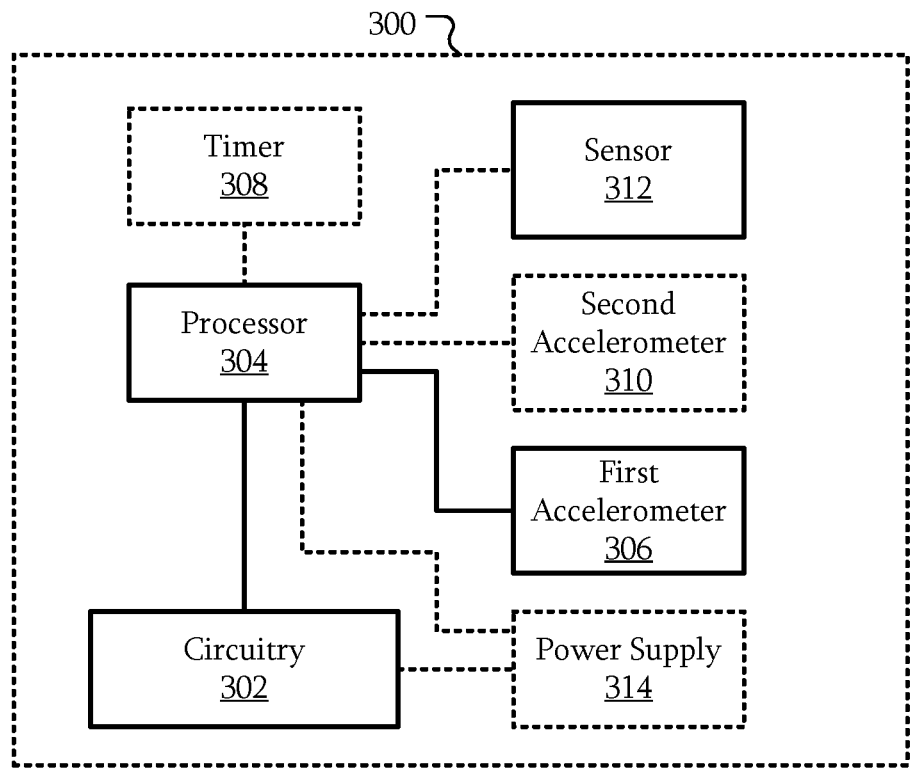
FIG. 6 is a block diagram of a device with an accelerometer according to some embodiments.

FIG. 6 is a block diagram of a device with an accelerometer according to some embodiments. The device 300 may include circuitry similar to the detectors 100 described above. For example, the device 300 includes a processor 304 and a first accelerometer 306 similar to the processor 104 and first accelerometer 106 described above. In some embodiments, the device 300 may include a timer 308, a second accelerometer 310, one or more sensors 312, and a power supply 314 similar to the timer 108, a second accelerometer 110, one or more sensors 112, and a power supply 114 described above. The operation of the device 300 with such circuitry may be similar to the operations described above.

The device 300 includes circuitry 302 appropriate to the type of the device 300. Accordingly, the circuitry 302 may be different from the detector circuitry 102. For example, the device 300 may include a laptop, a mobile communication device, a tablet computer, portable medical equipment, or the like. In some embodiments, the device is part of a crash detection or reporting system of a vehicle. The circuitry 302 may include the circuitry that are part of such devices.

Figure 7:
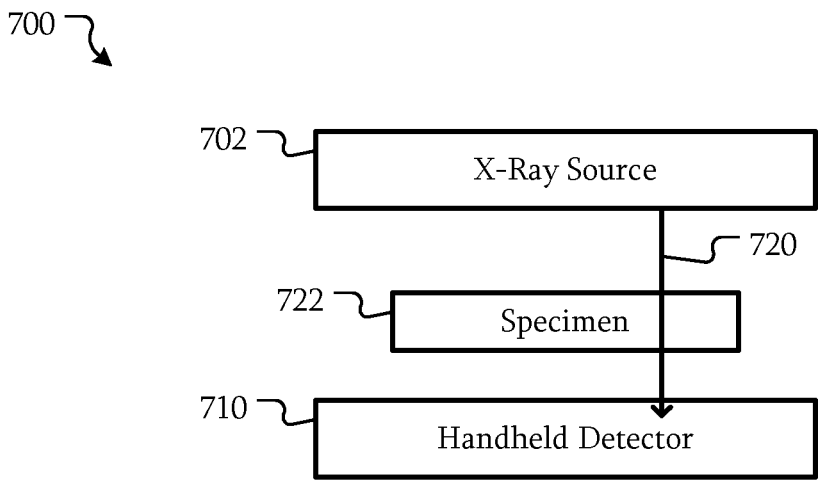
FIG. 7 is a block diagram of a 2D x-ray imaging system according to some embodiments.

FIG. 7 is a block diagram of a 2D x-ray imaging system according to some embodiments. The imaging system 700 includes an x-ray source 702 and a handheld detector 710. The handheld detector 710 may include a detector 100 as described above. The x-ray source 702 is disposed relative to the handheld detector 710 such that x-rays 720 may be generated to pass through a specimen 722 and detected by the handheld detector 710. After an operation, the handheld detector 710 may be moved to another location. In some embodiments, the handheld detector 710 is part of a medical imaging system. In other embodiments, the 2D x-ray imaging system may include a portable vehicle scanning system as part of a cargo scanning system.

Some embodiments include a handheld detector 100, comprising: detector circuitry 102 configured to convert incident radiation into electrical signals; a processor 104 coupled to the detector circuits; and an accelerometer 106 coupled to the processor 104; wherein the processor 104 is configured to activate from a low power state in response to a first acceleration event detected by the accelerometer 106.

In some embodiments, the processor 104 is configured to record a time of the first acceleration event.

In some embodiments, the processor 104 is configured to record a time of a second acceleration event after the first acceleration event; and generate a free-fall time based on the time of the first acceleration event and the time of the second acceleration event.

In some embodiments, the first acceleration event is an event when an acceleration sensed by the accelerometer 106 changes by a threshold.

In some embodiments, the accelerometer 106 is referred to as a first accelerometer 106, the handheld detector 100 further comprising: a second accelerometer 110 having a greater measurement range than the first accelerometer 106; wherein the processor 104 is configured to activate the second accelerometer 110 in response to the first acceleration event.

In some embodiments, a thickness of the handheld detector 100 is less than about 15 mm.

In some embodiments, the handheld detector 100 further comprises at least one of a temperature sensor, a humidity sensor, gyroscope, a touch sensor, and a rangefinder coupled to the processor 104.

In some embodiments, the handheld detector 100 further comprises a rangefinder coupled to the processor 104; wherein the processor 104 is configured to activate the rangefinder from a low power state in response to the first acceleration event and measure a distance using the rangefinder.

In some embodiments, the handheld detector 100 further comprises a power supply 114 configured to supply power to the detector circuitry 102; wherein the processor 104 is configured to disconnect or disable the power supply 114 in response to the first acceleration event.

Some embodiments include a method, comprising: sensing a first acceleration event by a first accelerometer 106 of a handheld detector 100 while a processor 104 of the handheld detector 100 is in a low power state; activating the processor 104 in response to the first acceleration event; and recording a time of the first acceleration event.

In some embodiments, the method further comprises sensing a second acceleration event by the first accelerometer 106; measuring a time between the first acceleration event and the second acceleration event; and determining a status of the handheld detector 100 in response to the time between the first acceleration event and the second acceleration event.

In some embodiments, wherein determining the status of the handheld detector 100 comprises: characterizing the second acceleration event as an impact if the time between the first acceleration event and the second acceleration event exceeds a threshold.

In some embodiments, the method further comprises activating a second accelerometer 110 in response to the first acceleration event; and sensing a second acceleration event by the second accelerometer 110; wherein the second accelerometer 110 has a greater measurement range than the first accelerometer 106.

In some embodiments, the method further comprises characterizing the second acceleration event as an impact if a magnitude of the second acceleration event exceeds a threshold.

In some embodiments, the threshold is a maximum of a measurement range of the second accelerometer 110.

In some embodiments, the method further comprises characterizing the second acceleration event as not an impact if a magnitude of the second acceleration event is less than a threshold.

In some embodiments, the method further comprises activating at least one sensor including at least one of temperature sensor, a humidity sensor, gyroscope, a touch sensor, and a rangefinder in response to the first acceleration event; and recording data from the at least one sensor after the first acceleration event.

In some embodiments, the method further comprises disabling a power supply 114 of the handheld detector 100 in response to the first acceleration event.

Some embodiments include a handheld detector, comprising: means for processing; means for detecting acceleration events of a handheld detector while the means for processing is in a low power state; means for activating the means for processing in response to a first acceleration event of the acceleration events; and means for recording a time of the first acceleration event. Examples of the means for processing include the processor 104. Examples of the means for activating the means for processing include interrupt circuitry and the first accelerometer 106 described above. Examples of the means for recording a time include the processor 304 and memory described above.

In some embodiments, the handheld detector further comprises means for measuring a time between the first acceleration event and a second acceleration event of the acceleration events; and means for determining a status of the handheld detector in response to the time between the first acceleration event and the second acceleration event. Examples of the means for measuring a time between the first acceleration event and a second acceleration event include the timer 108 and the processor 104 described above. Examples of the means for determining a status of the handheld detector include the processor 104.

Although the structures, devices, methods, and systems have been described in accordance with particular embodiments, one of ordinary skill in the art will readily recognize that many variations to the particular embodiments are possible, and any variations should therefore be considered to be within the spirit and scope disclosed herein. Accordingly, many modifications may be made by one of ordinary skill in the art without departing from the spirit and scope of the appended claims.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the claims beginning with claim [x] and ending with the claim that immediately precedes this one," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed to cover the corresponding structure, material, or acts described herein and equivalents thereof in accordance with 35 U.S.C. § 112 ¶ 6. Embodiments of the invention in which an exclusive property or privilege is claimed are defined as follows.

The invention claimed is:

1. A handheld imaging detector, comprising:
   detector circuitry configured to convert incident x-ray radiation into an x-ray image;
   a processor coupled to the detector circuits; and
   an accelerometer coupled to the processor;
   a power supply configured to supply power to the detector circuitry;
   wherein the processor is configured to:
      activate from a low power state in response to a first acceleration event detected by the accelerometer; and
      record a time of the first acceleration event; and
      disconnect or disable the power supplied to the detector circuitry while maintaining power supplied to other circuitry in response to the first acceleration event.

2. The handheld x-ray imaging detector of claim 1, wherein the processor is configured to:
   record a time of a second acceleration event after the first acceleration event; and
   generate a free-fall time based on the time of the first acceleration event and the time of the second acceleration event.

3. The handheld x-ray imaging detector of claim 1, wherein the first acceleration event is an event when an acceleration sensed by the accelerometer changes by a threshold.

4. The handheld x-ray imaging detector of claim 1, wherein the accelerometer is referred to as a first accelerometer, the handheld detector further comprising:
   a second accelerometer having a greater measurement range than the first accelerometer;
   wherein the processor is configured to activate the second accelerometer in response to the first acceleration event.

5. The handheld x-ray imaging detector of claim 4, wherein a thickness of the handheld detector is less than 16 mm.

6. The handheld x-ray imaging detector of claim 1, further comprising at least one of a temperature sensor, a humidity sensor, gyroscope, a touch sensor, and a rangefinder coupled to the processor.

7. The handheld x-ray imaging detector of claim 1, further comprising:
   a rangefinder coupled to the processor;
   wherein the processor is configured to activate the rangefinder from a low power state in response to the first acceleration event and measure a distance using the rangefinder.

8. A method, comprising:
   sensing a first acceleration event by a first accelerometer of a handheld x-ray detector while a processor of the handheld x-ray detector is in a low power state;
   activating the processor in response to the first acceleration event;
   recording a time of the first acceleration event; and
   disconnecting or disabling the power supplied to detector circuitry of the handheld x-ray detector while maintaining power supplied to other circuitry of the handheld x-ray detector in response to the first acceleration event.

9. The method of claim 8, further comprising:
   sensing a second acceleration event by the first accelerometer;
   measuring a time between the first acceleration event and the second acceleration event; and determining a status of the handheld x-ray detector in response to the free-fall time between the first acceleration event and the second acceleration event.

10. The method of claim 9, wherein determining the status of the handheld x-ray detector comprises:

characterizing the second acceleration event as an impact if the time between the first acceleration event and the second acceleration event exceeds a threshold.

11. The method of claim 8, further comprising:

activating a second accelerometer in response to the first acceleration event; and sensing a second acceleration event by the second accelerometer;

wherein the second accelerometer has a greater measurement range than the first accelerometer.

12. The method of claim 11, further comprising:

characterizing the second acceleration event as an impact if a magnitude of the second acceleration event exceeds a threshold.

13. The method of claim 12, wherein the threshold is a maximum of a measurement range of the second accelerometer.

14. The method of claim 12, further comprising:

characterizing the second acceleration event as not an impact if a magnitude of the second acceleration event is less than a threshold.

15. The method of claim 8, further comprising:

activating at least one sensor including at least one of temperature sensor, a humidity sensor, gyroscope, a touch sensor, and a rangefinder in response to the first acceleration event; and recording data from the at least one sensor after the first acceleration event.

16. A handheld detector, comprising:

means for processing;

means for detecting acceleration events of a handheld x-ray detector while the means for processing is in a low power state;

means for activating the means for processing in response to a first acceleration event of the acceleration events;

means for recording a time of the first acceleration event: and means for disconnecting or disabling the power supplied to detector circuitry of the handheld x-ray detector while maintaining power supplied to other circuitry of the handheld x-ray detector in response to the first acceleration event.

17. The handheld detector of claim 16, further comprising:

means for measuring a time between the first acceleration event and a second acceleration event of the acceleration events; and means for determining a status of the handheld x-ray detector in response to the time between the first acceleration event and the second acceleration event.

* * * * *